United States Patent
Rooney

(10) Patent No.: US 6,945,946 B2
(45) Date of Patent: Sep. 20, 2005

(54) METHOD AND APPARATUS FOR THE TREATMENT OF PLANTAR ULCERS AND FOOT DEFORMITIES

(75) Inventor: John E. Rooney, 24 Windsor Dr., Oakbrook, IL (US) 60523

(73) Assignee: John E. Rooney, Oakbrook, IL (US)

( * ) Notice: Subject to any disclaimer, the term of this patent is extended or adjusted under 35 U.S.C. 154(b) by 553 days.

(21) Appl. No.: 10/150,693

(22) Filed: May 17, 2002

(65) Prior Publication Data

US 2003/0216675 A1 Nov. 20, 2003

(51) Int. Cl.[7] .................................................. A61F 5/00
(52) U.S. Cl. ........................................ 602/27; 128/882
(58) Field of Search ............................... 602/23, 27–29, 602/5–8; 128/882

(56) References Cited

U.S. PATENT DOCUMENTS

| | | | |
|---|---|---|---|
| 3,916,886 A | | 11/1975 | Rogers |
| 4,184,273 A | * | 1/1980 | Boyer et al. ................. 36/131 |
| 4,351,324 A | * | 9/1982 | Bronkhorst .................. 602/27 |
| 4,641,639 A | * | 2/1987 | Padilla ........................ 602/23 |
| 5,197,942 A | * | 3/1993 | Brady .......................... 602/5 |
| 5,226,245 A | | 7/1993 | Lamont |
| 5,368,551 A | * | 11/1994 | Zuckerman ................... 602/23 |
| 5,370,604 A | * | 12/1994 | Bernardoni .................. 602/27 |
| 5,571,077 A | | 11/1996 | Klearman et al. |
| 5,762,622 A | | 6/1998 | Lamont |
| 5,797,862 A | | 8/1998 | Lamont |
| 5,817,041 A | * | 10/1998 | Bader .......................... 602/23 |
| 5,827,210 A | * | 10/1998 | Antar et al. .................. 602/23 |
| 5,833,639 A | * | 11/1998 | Nunes et al. ................. 602/23 |
| 5,853,380 A | | 12/1998 | Miller |
| 6,083,185 A | | 7/2000 | Lamont |
| 6,228,044 B1 | * | 5/2001 | Jensen et al. ................ 602/27 |
| 6,361,514 B1 | * | 3/2002 | Brown et al. ................. 602/23 |
| 6,572,571 B2 | * | 6/2003 | Lowe ............................ 602/5 |

* cited by examiner

*Primary Examiner*—Gregory L. Huson
*Assistant Examiner*—Huong Q. Pham
(74) *Attorney, Agent, or Firm*—John E. Rooney

(57) ABSTRACT

A custom-made ankle/foot orthosis for the treatment of patients having plantar ulcers is disclosed, which comprises a rigid L-shaped support member and a rigid anterior support shell hingedly articulated to the L-shaped support member. The plantar portion of the L-shaped member further comprises at least one ulcer-protecting hollow spatially located for fitted placement in inferior adjacency to a user's plantar ulcer, thus allowing the user to transfer the user's weight away from the plantar ulcer and facilitating plantar ulcer treatment. The anterior support shell is designed for lateral hinged attachment to the L-shaped member to take advantage of medial tibial flare structure for enhancing the weight-bearing properties of the disclosed orthosis. A flexible, polyethylene hinge member hingedly attaches the anterior support shell to the L-shaped member and securing straps securely attach the anterior support shell in fixed, weight-bearing relation about the proximal, anterior portion of the user's lower leg.

17 Claims, 4 Drawing Sheets

METHOD AND APPARATUS FOR THE TREATMENT OF PLANTAR ULCERS AND FOOT DEFORMITIES

BACKGROUND OF THE INVENTION

1. Field of the Invention

The present invention relates generally to an apparatus for the treatment of foot conditions, and more particularly, to an orthosis constructed to unload weight off of an affected area of the foot thus aiding in the healing of foot conditions. In its most common usage, the present invention relates to an orthosis for the treatment of diabetic plantar ulcers, whereby body weight is borne by the orthosis to aid in the healing of this plantar skin condition.

2. Description of the Prior Art

Foot ulcers represent one of the most notable risk factors for lower extremity amputations in persons diagnosed with diabetes mellitus. Persons diagnosed with diabetes are typically classified as slow healers and are prone to debilitating foot ulcers due to both neurologic and vascular complications. Peripheral neuropathy can cause altered or complete loss of tactile sensation in the foot and/or leg, and in this regard, the diabetic patient with advanced neuropathy tends to loose the ability to discriminate between sharp-dull tactile sensation. Accordingly, any cuts or trauma to the foot of a diabetic patient with advanced neuropathy often go unnoticed for lengthy periods of time. At present, there is no known cure for neuropathy, although strict control over glucose levels has been shown to slow the progression of the neuropathy.

Further, a deformity commonly known as "charcot foot" occurs as a result of decreased sensation. Patients with "normal" tactile sensation in their feet automatically determine when too much pressure is being placed on an area of the foot. Once identified, the human body instinctively shifts position to relieve the stress. A patient with advanced neuropathy looses this important mechanism. As a result, tissue ischemia and necrosis may occur leading to plantar ulcers. Microfractures in the bones of the foot go unnoticed and untreated, resulting in disfigurement, chronic swelling and additional bony prominences.

Microvascular disease is an additional problem for diabetic patients, which can also lead to foot ulcers. It is well known that diabetes often results in a narrowing of smaller arteries, which narrowing cannot be resolved surgically. This microvascularization thus further prompts the diabetic patient to adhere to a strict glucose level regimen, maintain an ideal body weight and cease tobacco smoking in an attempt to reduce the onset of microvascular disease.

Should a diabetic patient develop a plantar ulcer, for whatever reason, treatment options are generally limited to a two-fold treatment plan. In the first instance, the prime objective is to obtain wound closure, which eliminates a portal of entry for bacterial invasion and development of limb-threatening infection. In the second instance, a further objective is to allow for a reduction in sited foot pressures or the "offloading" of tissues. In this regard, protective orthotic footwear has been shown to lower sited foot pressures and further has been shown to contribute to the healing and closing of wounds. Moreover, once a given plantar ulcer has been effectively closed, protective orthotic footwear has been shown to prevent the reoccurrence of plantar ulcers. Orthotic footwear has thus become an area of special interest to a number of industries reliant on the development of treatment devices for medical conditions. Accordingly, orthotic devices for the treatment of plantar ulcers and other foot abnormalities have been developed and are known in the prior art. Known orthotic devices for the treatment of plantar ulcers and other foot abnormalities, however, suffer from a number of deficiencies, several of which are described hereinafter.

U.S. Pat. No. 6,228,044('044 Patent), which issued to Jensen et al., discloses Methods and Apparatus for Treating Plantar Ulcers. This disclosure teaches a temporarily worn leg brace which comprises a pair of rigid shells, a fastening system for joining the shells together to form a unified brace and a combination of bladders which engage the patient's leg and tarsal region to off-weight the plantar surface, prevent plantar flexing and minimize shearing forces to the plantar surface. The volume of the bladders may be adjusted to maintain a uniform pressure between the bladders and the patient's leg. In addition to providing a means for off-weighting the plantar surface of a patient's foot, the brace is reusable and adjustable to accommodate changes in a patient's leg size. The '044 Patent does not disclose the use of a permanent orthosis, which may be easily worn to heal and close a plantar ulcer, and additionally, to maintain the plantar surface in a healed unulcerated state. Further, the '044 Patent does not disclose an orthosis, which may be easily donned and inserted inside a patient's modified street shoe.

U.S. Pat. No. 5,226,245('245 Patent); U.S. Pat. No. 5,762,622('622 Patent); U.S. Pat. No. 5,797,862('862 Patent); and U.S. Pat. No. 6,083,185('185 Patent), all of which issued to Lamont, disclose boot structures for use in the treatment of plantar conditions. In this regard, the '245 Patent discloses a Protective Boot Structure, which is designed for patients with arterial disease. The boot structure comprises a separate fluid-containing cushion which can be attached in a variety of positions on or in the boot to provide support for a patient's foot and leg primarily when bed-ridden, though a modest amount of ambulatory use is contemplated. The '622 Patent discloses a Medical Boot with Unitary Splint. This invention comprises a relatively soft boot component having a foot portion, a leg portion, and a relatively hard plastic splint formed with a foot portion and a leg portion. The foot portion of the splint is mounted inside the boot and the leg portion of the splint is outside the rear surface of the boot. The '862 Patent discloses a Medical Boot for Patient with Diabetic Foot. This invention is also designed for patients with arterial disease and comprises an insole formed with a heat-activated material to form a permanent impression of the bottom of the patient's foot. The insole is adapted for removable placement in a medical boot. The '185 Patent discloses a Medical Boot for Patient with Diabetic Foot. This disclosure details a liner for use with the invention disclosed in the '245 Patent and comprises a cushion placed inside a medical boot against an upper rear portion of the boot, to promote flotation support for the wearer's ankle when the cushion includes a soft midsection panel adapted to engage the ankle rear surface. A deformable fluid-containing pouch is removably disposed in a hollow interior space within the panel to provide ankle support. The pouch can be removed through a rear access opening that is normally closed a by a zipper means for closure.

These patents, which issued to Lamont, do not disclose the use of a permanent orthosis, which may be easily worn to heal and close a plantar ulcer, and additionally, to maintain the plantar surface in a healed unulcerated state. Further, the Lamont disclosures fail to disclose an orthosis, which may be easily donned and inserted inside a patient's modified street shoe.

U.S. Pat. No. 5,197,942('942 Patent), which issued to Brady, discloses a Customized Foot Orthosis. This orthosis comprises a brace having at least a back portion and a sole portion, an aperture extending through the sole portion and means for fastening the orthosis securely to a patient's foot and lower leg. The aperture is positioned to correspond with the location of the ulcerated site on a patient's foot, thus relieving pressure from the ulcerated site when a patient's foot is weight-bearing, thereby permitting a patient to be mobile while simultaneously assisting in the aeration and healing of the ulcerated site. The '942 Patent, does not disclose the use of a permanent orthosis, which may be easily worn to heal and close a plantar ulcer, and additionally, to maintain the plantar surface in a healed unulcerated state. Further, the '942 Patent fails to disclose an orthosis, which may be easily donned and inserted inside a patient's modified street shoe.

U.S. Pat. No. 5,833,639('639 Patent), which issued to Nunes et al., discloses a Short Leg Walker. This invention teaches and describes a short leg walker comprising a rigid sole and calf shell and an articulated rigid skin and dorsal shell. The shells are padded at selected locations with a non-inflatable padding such as foam or fiber padding and at other locations with an inflatable bladder and a second bladder between the inflatable bladder and the limb of the patient. The second bladder is responsive to deforming pressure exerted on it and will maintain its support of the limb when the pressure is removed. This construction is intended to be used to immobilize the foot, lower leg and ankle in lieu of a plaster of Paris cast, (See, Col. No. 1, Line Nos. 10–14) and no teaching is found for the treatment of plantar ulcers. The '639 Patent, thus, does not disclose the use of a permanent orthosis, which may be easily worn to heal and close a plantar ulcer, and additionally, to maintain the plantar surface in a healed unulcerated state. Further, the '639 Patent fails to disclose an orthosis, which may be easily donned and inserted inside a patient's modified street shoe.

U.S. Pat. No. 5,370,604('604 Patent), which issued to Bernardoni, discloses a Kinesthetic Ankle-Foot Orthosis. This invention has been designed primarily to treat the condition commonly known as "drop foot" in which a patient is unable to lift the patient's foot. The orthosis described in the '604 Patent comprises a lower portion, which contacts the plantar surface of the foot. The lower portion is continuous with an upper portion, which contacts the posterior surface of the lower leg. The lower and upper portions are attached to a patient's leg by a strap extending around the proximal portion of a patient's lower leg. The lower portion of the orthosis further comprises apertures at selected locations to allow selected portions of the foot to contact the floor while the orthosis is being used. The '604 Patent does not disclose the use of a permanent orthosis, which may be easily worn to heal and close a plantar ulcer, and additionally, to maintain the plantar surface in a healed unulcerated state. Further, the '604 Patent fails to disclose an orthosis, which may be easily donned and inserted inside a patient's modified street shoe.

U.S. Pat. No. 5,853,380('380 Patent), which issued to Miller, discloses a Soft Ankle/Foot Orthosis. This invention comprises an upper portion and a lower portion formed of layers of soft material to surround the foot and lower portions of the leg. The layers of soft material thus form a split shell, which is sized and shaped to receive the lower leg and foot of a person desirous of orthotic treatment. One or more reinforcing stays are fixedly sandwiched between the inner layer and the outer layer to assist in holding the shell in its molded shape. The rigid reinforcing stay may be sandwiched between the layers of soft material in a generally L-shape to provide additional support to the leg and foot. A plurality of releasable fasteners is used to hold the shell in place on the wearer. It is further noted that the '380 Patent does not disclose the use of a permanent orthosis, which may be easily worn to heal and close a plantar ulcer, and additionally, to maintain the plantar surface in a healed unulcerated state. Further, the '380 Patent fails to disclose an orthosis, which may be easily donned and inserted inside a patient's modified street shoe.

U.S. Pat. No. 4,351,324('324 Patent), which issued to Bronkhorst, discloses a Therapeutic Walking Device. This device is designed to reduce the tendency of persons with cerebral palsy to walk on the balls of their feet. The device comprises a foot section and a calf section formed at a 90-degree angle. The foot section has a heel support and a toe support, which supports are spaced so as to prevent pressure from being exerted on the sole of the foot between the heel and toes. The leg section is strapped about the calf of the user's leg. The '324 Patent does not disclose the use of a permanent orthosis, which may be easily worn to heal and close a plantar ulcer, and additionally, to maintain the plantar surface in a healed unulcerated state. Further, the '324 Patent fails to disclose an orthosis, which may be easily donned and inserted inside a patient's modified street shoe.

U.S. Pat. No. 3,916,886('886 Patent), which issued to Rogers, discloses a Preformed Self-Conforming Drop Foot Brace. This brace comprises an upper calf portion and lower foot portion and is of such a structure that both the foot of the user and the lower portion of the brace maybe disposed in a shoe without alteration or modification of the latter. It is noted that due to the conforming nature of the brace, it is inconspicuous when worn for the upper portion of the brace may be situated within the confines of the trouser leg of a user, and the lower portion of the brace may be situated within a street shoe. The '886 Patent, however, does not disclose the use of a permanent orthosis, which may be easily worn to heal and close a plantar ulcer, and additionally, maintain the plantar surface in a healed unulcerated state.

U.S. Pat. No. 5,571,077('077 Patent), which issued to Klearman et al., discloses a Self-Supporting Foot Orthosis with Pivotally Mounted Cover. This invention comprises a generally L-shaped rigid shell for receiving a patient's lower leg and foot. The rigid shell further comprises a lower, correspondingly shaped rigid cover articulated at the rearmost portion of the upwardly extending part of the first shell. The cover may be pivoted downward, that is, away from the plantar portion of the first shell to provide a support that will elevate the patient's foot when the patient is lying down and which will cover the sole when it is pivoted toward the plantar portion of the foot. Apertures in the first shell allow the patient's foot to be treated and inspected when the cover is pivoted away from the plantar portion of the foot. The '077 Patent does not disclose the use of a permanent orthosis, which may be easily worn to heal and close a plantar ulcer, and additionally, maintain the plantar surface in a healed unulcerated state. Further, the '077 Patent fails to disclose an orthosis, which may be easily donned and inserted inside a patient's modified street shoe.

It will thus be seen from a review of the foregoing prior art references that the prior art thus perceives a need for a permanent orthosis, which may electively be worn throughout one's life, which may be easily donned and inserted inside a patient's modified street shoe. In this regard, it has been repeatedly shown that the cited patent disclosures do not disclose the use of a permanent orthosis, which may be easily worn to heal and close a plantar ulcer, and additionally, maintain the plantar surface in a healed, unulcerated state. Further, the cited prior art fails to disclose an orthosis for the treatment of plantar ulcers comprised primarily of molded polypropylene or a similar polyester resin, which may be easily donned and inserted inside a patient's modified street shoe. What is needed is a treatment device to aid in supporting the lower leg and foot of patients who have been diagnosed with diabetic neuropathic, charcot joint and plantar ulcers with our without foot deformity. Current treatment modalities for plantar ulcers include reducing weight-bearing events through the use of crutches or total contact casts or wheelchairs. Additionally, surgical intervention is often employed. In this regard, it is noted that many ulcerated patients undergo surgery to remove the infected ulcer through partial foot amputation or to remove prominent bony areas that cause pressure problems. Typically, many of these patients will either develop plantar ulcers in a new area of the foot or the patient will refrain from walking so as to prevent any new ulcers. Often, after surgery, the patient's gait is affected due to missing bone structure in the foot region. None of the aforementioned remedies, however, offer a permanent solution to unloading or relieving pressure at the ulcer site.

SUMMARY OF THE INVENTION

Accordingly, it is an object of the present invention to provide an ankle/foot orthosis, which is custom-made for a patient suffering from plantar ulcer conditions for permanent use. It is a further object of the present invention to provide such an orthosis with unique construction, which construction provides an orthosis easily donned and worn in combination with a modified shoe. It is a further object of the present invention to provide an orthosis, which allows for maximum support of a user's plantar foot surface. Still further, it is an object of the present invention to provide an effective treatment device for plantar ulcers, while stabilizing the ankle and plantar surface of the foot with attached custom alignment wedges, which provide balance and allow for a more normal gait. The present invention reduces pressure at the ulcer location and typically allows immediate ambulation upon its final fitting.

These and further objects are accomplished by the present invention which generally comprises a rigid, substantially L-shaped support member and a rigid anterior support shell hingedly articulated to the L-shaped support member. The L-shaped support member further comprises a substantially vertical, posterior support shell portion and a substantially horizontal, plantar support platform portion. The posterior support shell portion and plantar support platform portions are sized and shaped via state of the art casting and molding techniques to snugly receive the posterior portion of a user's lower leg and tarsal region, and the plantar portion of a user's foot. Proximally, the posterior support shell terminates in a proximal flared posterior shell brim. Distally, the posterior support shell terminates in a tarsal support structure, the tarsal support structure comprising a medial tarsal support portion, a lateral tarsal support portion, and a heel support portion intermediate the medial tarsal support portion and lateral support portion. Both the medial tarsal support portion and the lateral tarsal support portion extend in an anterior or ventral manner to a point intermediate the length of the plantar support platform. The orthosis is designed such that when a user dons the orthosis, the proximal flared posterior shell brim is located about ½ inch distally adjacent to the fibular head of the user's lower leg. The posterior support shell further comprises a circumferential corrugated rib structure intermediate the posterior support shell height for increasing the structural strength of the posterior support shell and to assist in guiding placement of an anterior support shell. The plantar support platform further comprises at least one ulcer-protecting hollow, which is spatially located for fitted placement in inferior adjacency to a user's diabetic plantar ulcer, thus allowing the user to transfer the user's weight away from the plantar ulcer and facilitating plantar ulcer treatment.

The anterior support shell is designed for lateral hinged attachment to the posterior support shell and receives the anterior, proximal portion of a user's lower leg when the anterior support shell is hingedly closed and secured. The anterior support shell has a corresponding proximal flared anterior shell brim and a distal flared anterior shell brim. The anterior support shell is designed so that when a user is fitted with the orthosis, the proximal flared anterior shell brim is also spatially located for fitted placement in distal adjacency to the fibular head of the user leg. The anterior support shell further comprises a plurality of securing strap-receiving loops securely attached to the outer anterior support shell surface for receiving a plurality of securing straps.

A flexible, polyethylene hinge member hingedly attaches the anterior support shell to the posterior support shell. The hinge member allows the orthosis to be fully opened to receive a patient's leg and foot and then may be simply and securely fastened to the patient by closing and securing the anterior support shell. The hinge member hingedly attaches the anterior support shell to the posterior support shell such that the proximal flared anterior shell brim and flared posterior shell brim lie in substantially the same plane and such that the distal flared anterior shell brim and circumferential corrugated rib structure lie in substantially the same plane. The circumferential corrugated rib structure is designed to increase the structural strength of the posterior support shell and further for guiding placement of the anterior support shell.

A plurality of securing straps is further disclosed. The securing straps each have an inner strap surface and an outer strap surface, where the outer strap surfaces further comprise hook and loop fastening means. The securing straps each having a posterior support shell attachment end and a securing strap feed end, which feed ends are fed through the securing strap receiving loops for securing the anterior support shell in fixed, weight-bearing relation about the proximal, anterior portion of the user's lower leg.

Additionally, posterior support shell padding may be attached to the inner posterior support shell surface for alleviating skin irritation of the posterior portion of a user's lower leg and tarsal region for maintaining total contact. In like manner, anterior support shell padding may be attached to the inner anterior support shell surface for alleviating skin irritation of the anterior, proximal portion of a user's lower leg for maintaining total contact and for relieving bony prominences. Further, plantar support platform padding may be attached to the plantar support platform for alleviating skin irritation of the plantar portion of a user's foot and for adjusting pressure points, as needed.

Once the configuration of the plantar portion of the orthosis is determined, the insole of a modifiable shoe customarily worn by the patient is ground out to conform to the contours of the plantar portion of the orthosis, thus allowing the patient to wear the shoe while avoiding undue pressure on portions of the plantar region having downwardly projecting bony prominences and ulcers.

BRIEF DESCRIPTION OF THE DRAWINGS

Other features of our invention will become more evident from a consideration of the following detailed description of our patent drawings, as follows.

DETAILED DESCRIPTION OF PREFERRED EMBODIMENT

Figure 2:
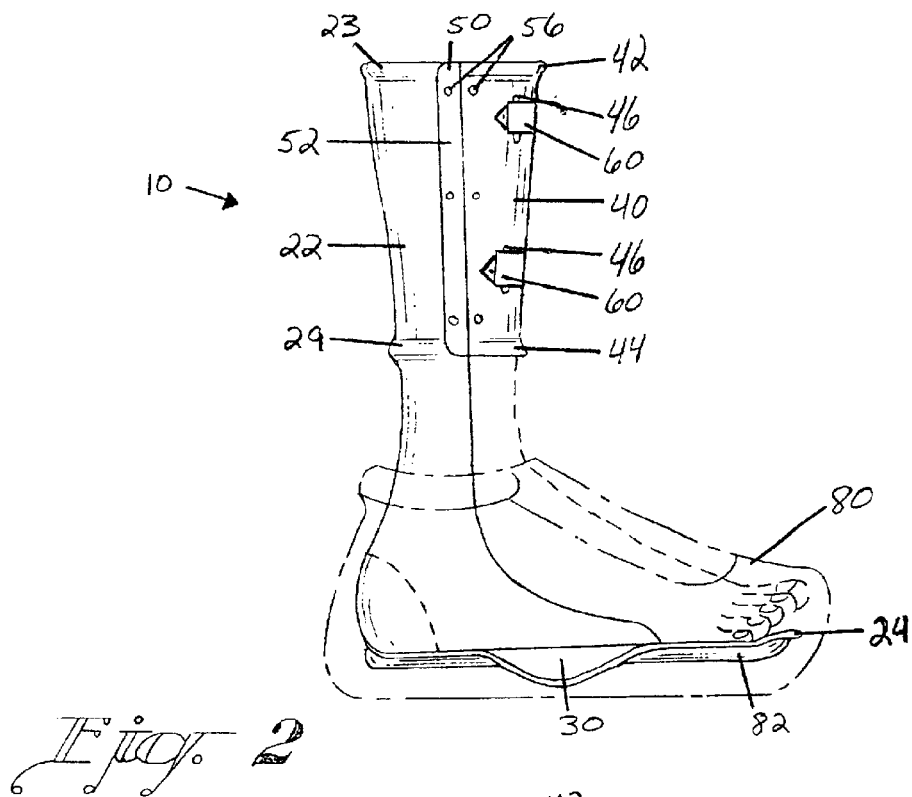
FIG. 2 is a right lateral view of a preferred embodiment of the present invention showing the invention applied to the right lower leg and foot of a user and showing, in partial sections, the positioning of the preferred embodiment within a shoe worn by the user.

Referring now to the drawings, the preferred embodiment of the present invention, namely, a custom-made orthosis 10 for the treatment of diabetic plantar ulcers is generally illustrated in FIGS. Nos. 1–7, inclusive. It is contemplated that custom-made orthosis 10 may be used in combination with a modified shoe 80 or other similar other footwear for concealing custom-made orthosis 10 from general public view, as shown in FIG. 2. In this regard, an orthotic system for treating plantar ulcers is contemplated, which system involves not only the fitting of custom-made orthosis 10 to the user, but also the insertion of custom-made orthosis 10 inside a modified shoe 80 or similar footwear. The orthotic system, or custom-made orthosis 10 used in combination with modified shoe 80, presents users with the option of utilizing an effective orthotic device without the social stigma often associated with readily apparent orthotic device use, as is often experienced with controlled ankle motion (CAM) walker usage. The contemplated orthotic system thus alleviates not only the user's plantar ulcer, but provides further relief from social stigmatization often associated with readily apparent orthotic device usage. In some cases, it should be noted that modified shoe 80 must be modified to accommodate custom-made orthosis 10, which modification is generally internal to modified shoe 80 and not readily apparent to passersby.

Custom-made orthosis 10 is designed generally for supporting the lower leg and foot a user who has been diagnosed with diabetic, neuropathic, charcot joint, plantar ulcers with or without foot deformity, or possibly blistered or callused portions of the user's foot. To this end, custom-made orthosis 10 generally comprises a rigid, or substantially rigid, substantially L-shaped support member 20 (as shown in FIG. Nos. 1, 4 and 5) formed from state of the art casting and molding techniques. L-shaped support member 20 is preferably comprised molded polypropylene of about 3/16 inch thickness or a similar polyester resin. It is noted that state of the art orthotics for the treatment of plantar ulcers have heretofore not been comprised of polypropylene and have not been constructed to be easily donned and inserted inside a modified street shoe. L-shaped support member 20 further comprises a substantially vertical, continuously-formed, posterior support shell 22 (as shown in FIG. Nos. 1, 2, 4, 5, 6 and 7) and a substantially horizontal, cotinuously-formed, plantar support platform 24 (as shown in FIG. Nos. 1, 2, 4, 5 and 6) formed as a Continuous integral Construction.

As shown, posterior support shell 22 has a posterior shell height, the dimension of which generally measures from the plantar region of the user's foot to a point distally adjacent to the fibular head region of the user's lower leg. As further shown, plantar support platform 24 has a platform length, the dimension of which generally measures from the posterior edge of a user's foot region to the anterior edge of the user's foot region. Posterior support shell 22 further comprises an inner posterior shell surface and an outer posterior shell surface. Posterior support shell 22 is sized and shaped to receive the posterior portion (or all posterior portions) of a user's lower leg and tarsal region as shown in FIG. No. 2. As further shown in FIG. No. 2, plantar support platform 24 is sized and shaped to support the plantar portion of a user's foot.

The posterior support shell height terminates proximally in a proximal flared posterior shell brim 23 (as shown in FIGS. Nos. 1, 2, 3, 4, 5 and 7) and the posterior support shell height terminates distally in a tarsal support structure 25 (as shown in FIGS. Nos. 1, 4 and 5). Tarsal support structure 25 generally comprises a medial tarsal support portion 26 (as shown in FIGS. Nos. 1 and 5), a lateral tarsal support portion 27 (as shown in FIGS. Nos. 1 and 4), and a heel support portion 28 (as shown in FIGS. Nos. 1, 4 and 5) intermediate the medial tarsal support portion and lateral support portion. Medial tarsal support portion 26 and lateral tarsal support portion 27 provide added structural strength to the juncture of posterior support shell 22 and plantar support platform 24, and further provide rigid structural support for the tarsal region, which prevents ankle joint inversion and eversion and, further, prevents dorsiflexion and plantar flexion. Custom-made orthosis 10, thus, is not generally recommended for user's requiring ankle range of motion as part of a treatment regimen. However, the tarsal region may be modified to allow for range of motion, as prescribed. As shown, medial tarsal support portion 25 and lateral tarsal support portion 26 extend ventrally to a point intermediate the platform length. Proximal flared posterior shell brim 23 is spatially located for fitted placement in distal adjacency to the fibular head of a user's lower leg. Posterior support shell 22 further comprises a circumferential corrugated rib structure 29 (as shown in FIGS. Nos. 1, 2, 4, 5 and 7) intermediate the posterior support shell height for increasing the structural strength of posterior support shell 22 and for guiding placement of an anterior support shell, which structure is described below.

Figure 1:
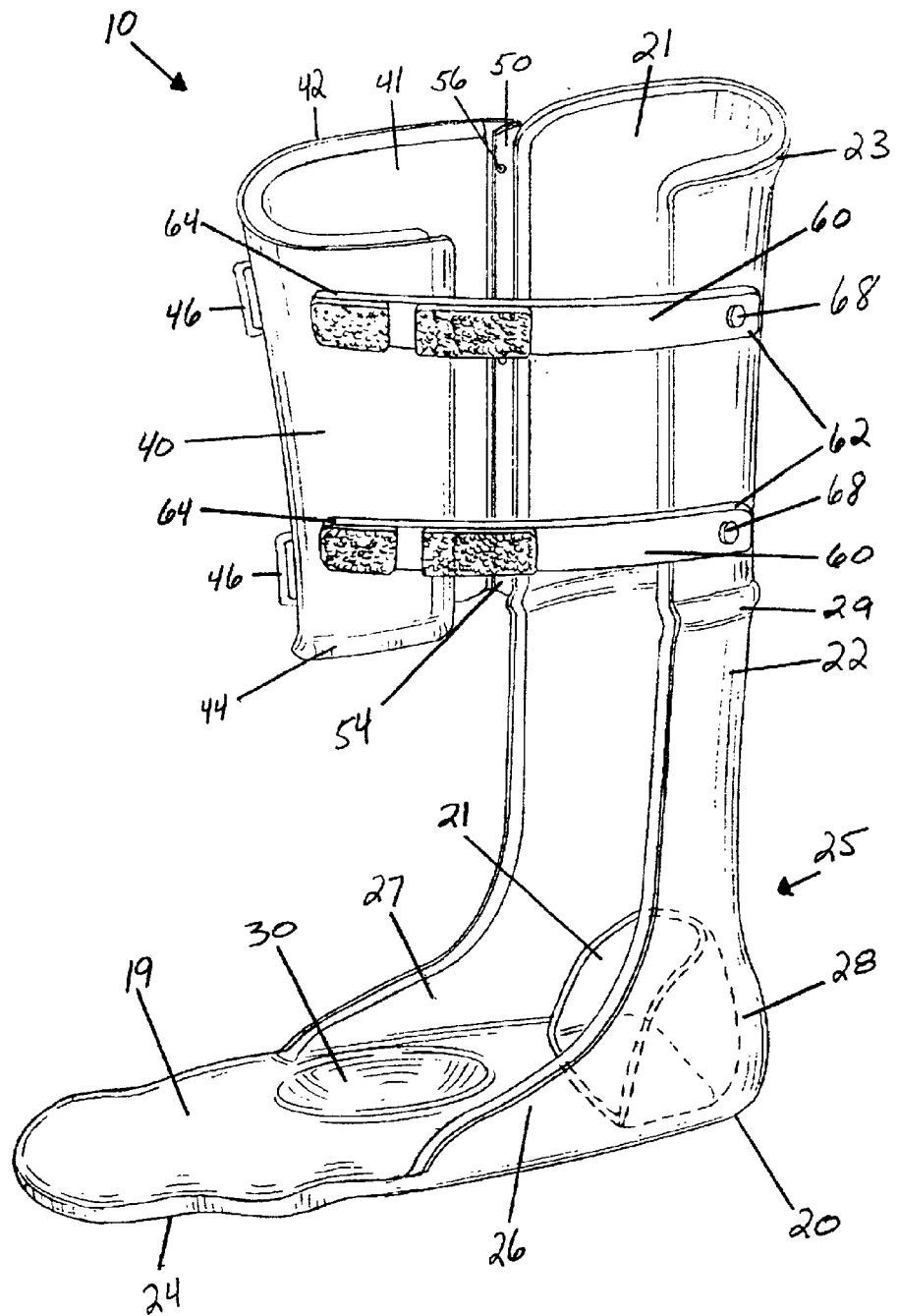
FIG. 1 is a perspective view of the preferred embodiment of the present invention, showing the anterior support shell in an opened state for receiving a user's lower leg and foot.

Plantar support platform 24 has a superior surface and an inferior surface and further comprises at least one ulcer-protecting hollow 30 as shown in FIGS. Nos. 1–7, inclusive. Further, plantar support platform is preferably contoured to conform to the patient's foot generally having a first anterior segment to support the patient's toes, a second anterior segment to support the metatarsal heads of the foot, an intermediate sole segment to support the arch of the foot and a posterior segment to support the heel of the foot. Ulcer-protecting hollow 30 is spatially located for fitted placement in inferior adjacency to a user's diabetic or other plantar ulcer. A typical location for ulcer-protecting hollow 30 is shown in FIG. 1, where plantar ulcers due to charcot joint collapse are typically found approximately the mid-length of user's foot on the lateral half of the plantar area. Ulcer-protecting hollow 30 thus provides a rigid shield or rigid pocket to breathably receive the plantar ulcer at the superior surface of plantar support platform 24. Notably, hollow 30 inherently has a superior hollow surface and an inferior hollow surface, the superior hollow surface being continuous with the superior platform surface and the inferior hollow surface being continuous with the inferior platform surface. It will be recalled that hollow 30 is designed for fitted placement in inferior adjacency to a user's diabetic plantar ulcer. In this regard, the superior hollow surface is preferably spaced from the user's diabetic plantar ulcer so as to promote healing thereof. Ulcer-protecting hollow 30 thus enables a user to transfer a user's weight away from the plantar ulcer when the inferior surface of plantar support platform 24 contacts stepping surfaces, thus facilitating plantar ulcer treatment, or the healing and closing (parenchymal regeneration) of an ulcerated site. When custom-made orthosis 10 is worn following ulcer closure, the prevention of further ulcers at the specific closed ulcer site is contemplated and achieved by ulcer-protecting hollow 30. Custom-made orthosis 10 further preferably comprises a rigid, or substantially rigid, anterior support shell 40 as shown in FIGS. Nos. 1–6, inclusive and as referred to above. support shell 40 is preferably designed for lateral hinged attachment to posterior support shell 22 and provides custom-made orthosis 10 with a rigid, weight-bearing area. In this regard, a lateral hinge attachment is to be preferred, since the medial tibial flare of the user's lower leg is typically a weight-bearing portion of the user's lower leg and medial closing securement reinforces this weight-bearing characteristic. The preferred lateral hinge attachment advantageously incorporates the natural form and function of the medial tibial flare into its preferred design. Anterior support shell 40 is preferably comprised of molded polypropylene of about ⅛ inch thickness or a similar polyester resin and has an inner anterior support shell surface and an outer anterior support shell surface. Anterior support shell 40 is designed to receive the anterior, proximal portion of a user's lower leg.

Anterior support shell 40 has a proximal flared anterior shell brim 42 (as shown in FIGS. Nos. 1–6, inclusive) and a distal flared anterior shell brim 44 (as shown in FIGS. Nos. 1–6, inclusive). Proximal flared anterior shell brim 42 is spatially located for fitted placement in distal adjacency to the fibular head of the user's leg. Anterior support shell 40 further comprises securing strap receiving structure, which preferably further comprises a plurality of securing strap receiving loops 46 (as shown in FIGS. Nos. 1–6, inclusive) securely attached to the outer anterior support shell surface. Securing strap-receiving loops 46 preferably comprise 2-inch metal buckle loop retainers. Receiving loops are preferably attached the outer surface of anterior support shell 40 using plastic chafe structures, which chafe structures are preferably riveted to the outer surface of anterior support shell 40, substantially as shown.

Custom-made orthosis 10 further preferably comprises hinge means for hingedly 15 attaching anterior support shell 40 to posterior support shell 22. Preferably, the hinge means is further defined by comprising a flexible polyethylene hinge member 50 (as shown in FIGS. Nos. 1, 2 and 4) for hingedly attaching anterior support shell 40 to posterior support shell 22. Hinge member 50 has an inner hinge surface, an outer hinge surface, and preferably, a hinge member thickness of about ¹⁄₁₆ inch. Hinge member 50 further has a posterior hinge portion 52 as shown in FIGS. Nos. 2, 4 and 7, and an anterior hinge portion 54 as shown in FIG. 1. The outer hinge surface of anterior hinge portion 52 is preferably securely fastened to the lateral most edge of the inner anterior support shell surface and the inner hinge surface of posterior hinge portion 54 is securely fastened to the lateral most edge of the outer posterior support shell surface. Preferably, copper rivets 56 (as shown in FIGS. Nos. 1, 2, 3, 4, 6 and 7) fasten hinge member 50 to anterior support shell 40 and posterior support shell 22. Excellent results have been found when SPEEDY brand rivets 56 are used in the installation of hinge member 50 as described. Hinge member 50 thus hingedly attaches anterior support shell 40 to posterior support shell 22 such that proximal flared anterior shell brim 42 and proximal flared posterior shell brim 23 lie in substantially the same, substantially horiztonal, plane and further such that distal flared anterior shell brim 44 and circumferential corrugated rib structure 29 lie in substantially the same, substantially horiztonal, plane.

In this last regard, it is noteworthy that circumferential corrugated rib structure 29 is preferably located at the distal calf muscle area. Not only does circumferential corrugated rib structure 29 add strength to posterior support shell 22, but further provides guiding placement of distal flared anterior support shell brim 44 of anterior support shell 40 .as shown in FIGS. Nos. 2, 4 and 5. Further, the plane in which the flared proximally-located shell brim structures lie is preferably located distally about ½ inch from the fibular head of the user's lower leg. Hinge member 50 further acts as a placement for anterior support shell 40 to prevent anterior support shell 40 from moving proximally or distally, which movement would throw off the actual alignment of the weight-bearing areas.

Figure 3:
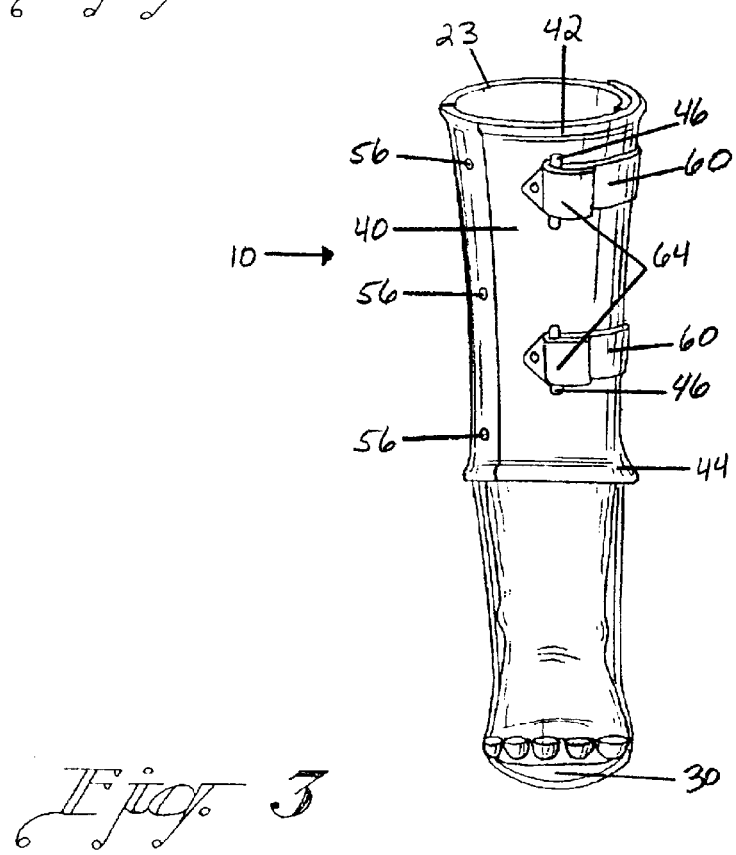
FIG. 3 is an anterior view of the preferred embodiment as attached to the right lower leg and foot of a user.
Figure 4:
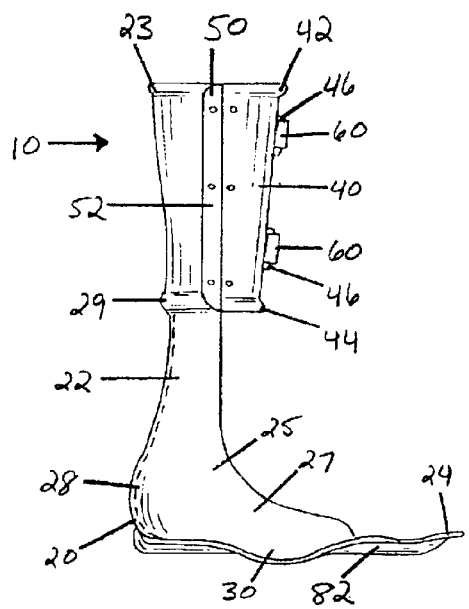
FIG. 4 is a right lateral view of a preferred embodiment in combination with a custom alignment wedge.
Figure 5:
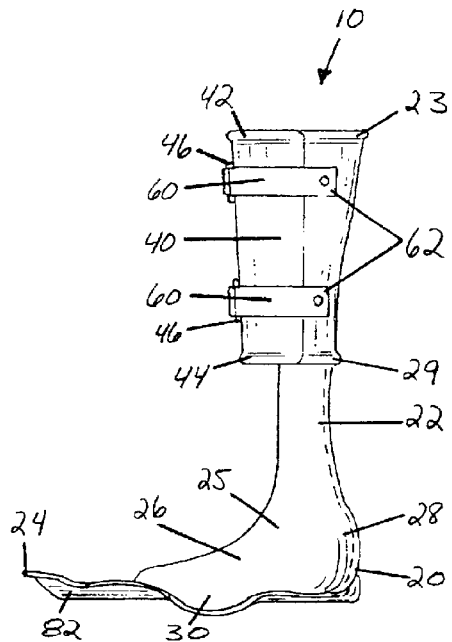
FIG. 5 is a right medial view of a preferred embodiment in combination with a custom alignment wedge.
Figure 6:
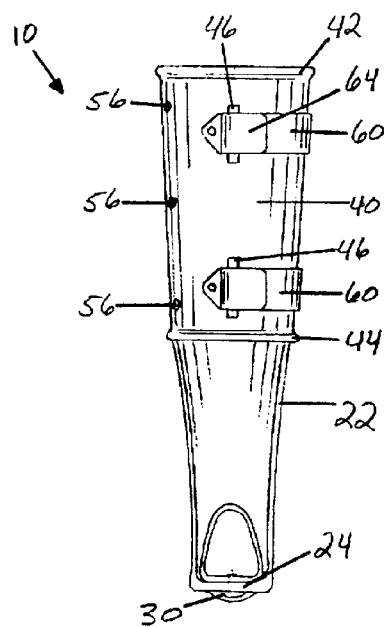
FIG. 6 is an anterior view of a preferred embodiment.
Figure 7:
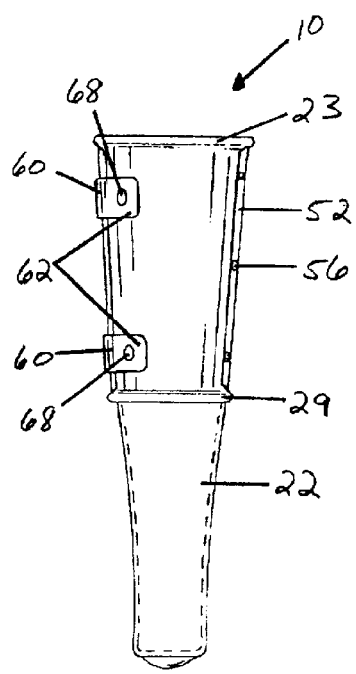
FIG. 7 is a posterior view of the preferred embodiment shown in FIG. 6.

Custom-made orthosis 10 further comprises securing means for securing anterior support shell 40 to posterior support shell 22 in fixed, weight-bearing relation about the anterior, proximal portion of a user's leg. In this regard, the securing means is defined by preferably comprising a plurality of securing straps 60 as shown in FIGS. Nos. 1–7, inclusive, which straps are preferably 2 inches in width. Securing strap length is dependent upon the needs of the individual user. Securing straps 60 each have an inner strap surface comprised primarily of nylon webbing and an outer strap surface. The outer strap surface is preferably comprised of hook and loop fastening means, which may be defined by preferably comprising VELCRO brand hook and loop structure. Securing straps 60 each further have a posterior support shell attachment end 62 as shown in FIGS. Nos. 1, 5 and 7 and a securing strap feed end 64 as shown in FIGS. Nos. 1, 3 and 6. Posterior support shell attachment ends 62 are securely fastened to the medial portion of posterior support shell 22. Preferably, posterior support shell attachment ends 62 are fastened to posterior support shell 22 by rivets 68, preferably comprised of copper. Excellent results have been achieved by using SPEEDY brand rivets 68 to secure posterior support shell attachment ends 62 to posterior support shell 22 in that installation is fast and easy. To secure anterior support shell 40 about the user's leg, securing strap feed ends 64 are each fed through securing strap receiving loops 46 and doubled back upon themselves for securing anterior support shell 40 in fixed, weight-bearing relation about the anterior, proximal portion of the user's lower leg. When anterior support shell 40 is secured about the anterior, proximal portion of the user's lower leg, the medial most edge of anterior support shell 40 preferably overlaps the medial most edge of posterior support shell 22 preferably about ¾ inch as shown in FIG. 3.

Custom-made orthosis 10 further preferably comprises posterior support shell padding 21 as shown in FIG. 1, which may be attached to the inner posterior support shell surface for alleviating skin irritation of the posterior portion of a user's lower leg and tarsal region and for maintaining total contact between a user's lower leg and the fitted orthosis. In this regard, it is contemplated that posterior support shell padding 21 may be typically attached to the inner posterior shell surface at proximal portions of posterior support shell 22 to alleviate frictional forces and sheer, and at the heel support portion of the tarsal support region to alleviate heel pumping and the resultant excessive skin irritation. It is to be further understood that when rivets 56 securely fasten the inner hinge surface of posterior hinge portion 54 to the lateral most edge of the outer posterior support shell surface, rivets 56 are hidden from view by being sandwiched between the inner posterior support shell surface and posterior support shell padding 21. Preferably, posterior support shell padding 21 comprises closed cell polyurethane padding.

Custom-made orthosis 10 further preferably comprises anterior support shell padding 41 as shown in FIG. 1, which is attached to the inner anterior support shell surface for generally preventing frictional forces and sheer, thus alleviating skin irritation of the anterior, proximal portion of a user's lower leg as well as for maintaining total contact. Anterior support shell padding 41 further provides bony relief. Preferably, anterior support shell padding 41 comprises closed cell polyurethane padding. Custom-made orthosis 10 further preferably comprises plantar support platform padding 19, which is attached to plantar support platform 24 for alleviating skin irritation of the plantar portion of a user's foot and for adjusting pressure points, as needed. Plantar support platform padding 19 preferably comprises an ⅛ inch or less closed cell polyurethane padding. Plantar support platform padding 19 may further comprise a raised arch portion, as required by the user.

It is noted that, given the state of the art, an orthosis comprised of polypropylene or a similar polyester resin for the treatment of plantar ulcers would not be recommended for use on a diabetic patient for the treatment of plantar ulcers. This is due to the current understanding in the prior art literature that polypropylene orthoses could cause sheering and skin breakdown of the diabetic patient thus creating a new pressure sore or decubitus ulcer on a user's leg. The present invention is comprised almost entirely of plastic as described. The exceptions to the materials composition are primarily the padded areas to help in applying or having weight distributed across the anterior support shell and plantar support platform of the foot region. Additionally, common art bladders may be used in conjunction with posterior support shell padding 21 to accommodate leg size variance within a given user. The present invention thus overcomes the state of the art insofar as a custom-made orthotic for use in the treatment of plantar ulcers is provided, which orthotic is comprised primarily of polypropylene plastic. Further, the described orthotic may easily be donned and worn inside of a modified shoe with typical internal modification.

Figure 8:
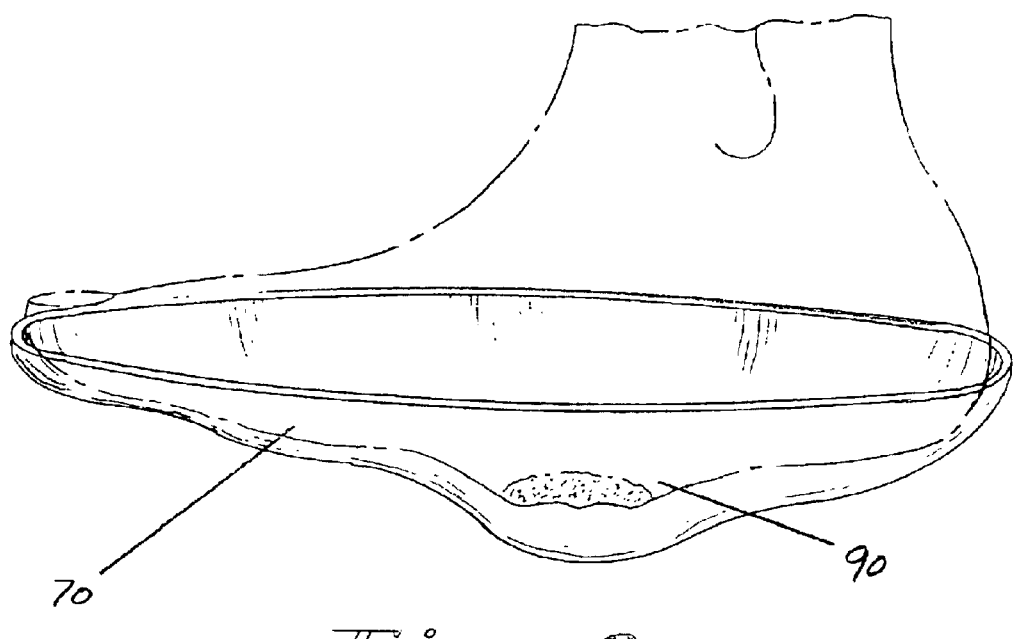
FIG. 8 is a perspective view of a clear plastic check socket for placement on a user's ulcerated foot.

Custom-made orthosis 10 is generally formed through common art practices where a cast is taken of the user's lower leg and foot, which cast is then removed from the user's lower leg and foot and filled in a typical fashion with a plaster liquid. The plaster liquid is then allowed to harden, leaving a replica or positive model of the user's foot and leg. At some point before the formation of L-shaped support member 20, a further inventive step involves the formation of a clear plastic check socket 70 from the positive model, which check socket 70 is shown in FIG. 8. Check socket 70 typically resembles plantar support platform 24 structurally, but is a preliminary form for plantar support platform 24. As indicated, check socket 70 is preferably comprised of a clear plastic and is then fitted to the plantar portion of a user's foot, which provides the manufacturer of custom-made orthosis 10 with a visual opportunity to make a detailed inspection of the plantar portion of a user's foot. Noting problematic portions of the check socket in relation to the positive model, particularly with regard to the weight-bearing areas of L-shaped support member 20, the manufacturer of custom-made orthosis 10 may more easily make modifications to the positive model before L-shaped support member 20 is finally formed. Custom-made orthosis 10 may be more confidently vacuum molded following the indicated check socket procedure to provide a more effective orthosis.

L-shaped support member 20 is typically molded first, and trimmed as needed. Anterior support shell 40 is typically molded after L-shaped support member and trimmed as needed. Once custom-made orthosis 10 is constructed as described, it may then be fitted into modified shoe 80 by grinding out an ulcer-protecting hollow receiving structure in the shoe insole to accommodate ulcer-protecting hollow 30. When custom-made orthosis 10 is to be utilized, the user may hingedly operate anterior support shell 40 to an open position. Thereafter, the user may position the user's foot with the user's heel in heel support portion 28 and with the user's plantar ulcer site 90 (as diagrammatically shown in FIG. 8) positioned at ulcer-protecting hollow 30.

Anterior support shell 40 is then secured to a user's lower leg by threading securing straps 60 through securing strap receiving loops 46 by pulling securing straps 60 taught and fastening securing straps 60 to themselves through the use of the hook and loop fastening means located on the outer strap surface of securing straps 60. The user may then insert the user's foot along with custom-made orthosis 10 into modified shoe 80 aligning ulcer-protecting hollow 30 into modified shoe 80, thus effectively receiving custom-made orthosis 10 and the user's foot. It is further contemplated that expedients such as custom alignment wedges 82, for example, heel or sole wedges, lateral or medial or both (which wedges are commonly used and understood by those skilled in the orthotic arts), may be attached in distal adjacency to the inferior surface of plantar support platform 24 to provide additional stability to custom-made orthosis 10 as shown in FIG. Nos. 2,4 and 5. An exemplary custom alignment wedge 82 is shown in FIG. Nos. 2, 4 and 5.

The reader will thus see that it is an object of the present invention to provide an ankle/foot orthosis, which may be custom-made for a patient suffering from plantar ulcer conditions for permanent use. It will be further seen that an object of the present invention to provide such an orthosis with unique construction, which construction provides an orthosis easily donned and worn in combination with a modified shoe. Still further, it will be seen that an object of the present invention to provide an orthosis, which allows for maximum support of a user's plantar foot surface. Yet further, it will be seen that the present invention provides an effective treatment device for plantar ulcers, while stabilizing the ankle and plantar surface of the foot with attached custom alignment wedges, which provide balance and allow for a more normal gait. The present invention reduces pressure at the ulcer location and typically allows immediate ambulation upon its final fitting.

It is contemplated that the orthosis for the treatment of plantar ulcers and foot deformities herein illustrated and described is used primarily for descriptive and illustrative purposes and should not be construed to limit the scope of concept application to the application as shown. For example, it is contemplated that the hinge means need not comprise a flexible polyethylene hinge member. So long as functional, unobtrusive hinge means hingedly attach anterior support shell 40 to posterior support shell 22, the primary objectives of the present invention may still be achieved. In this regard, hinge means comprising a flexible polyethylene hinge member preferably fulfills this function.

Further, it is contemplated that securing means for securing anterior support shell 40 in fixed, weight-bearing relation about the proximal portion of a user's lower leg need not comprise securing straps as described herein. So long as functional, unobtrusive securing means secure anterior support shell 40 in fixed, weight-bearing relation about the proximal portion of a user's lower leg, the primary objectives of the present invention may still be achieved. In this regard, securing means comprising securing straps in combination with securing straps receiving loops preferably fulfills this function.

It is contemplated that alterations and further modifications, as well as other and further applications of the principles of the present invention will occur to others skilled in the art to which the invention relates and, while differing from the foregoing, remain within the spirit and scope of the invention as herein described and claimed. Where means-plus-function clauses are used in the claims such language is intended to cover the structures herein performing the recited functions and not only structural equivalents, but equivalent structures as well. For the purposes of the present disclosure, two structures that perform the same function within an environment described above may be equivalent structures. Accordingly, although the invention has been described by reference to a preferred embodiment, it is not intended that the novel device be limited thereby, but that modifications thereof are intended to be included as falling within the broad scope and spirit of the foregoing disclosure, the following claims and the appended drawings.

I claim:

1. An orthotic combination for the treatment of diabetic plantar ulcers, the orthotic combination comprising:
at least one modified shoe, the modified shoe being custom-fitted for receiving an orthosis, the orthosis further comprising:
a rigid, substantially L-shaped support member, the L-shaped support member comprising a substantially vertical, posterior support shell and a substantially horizontal, plantar support platform, the posterior support shell having a posterior shell height and the plantar support platform having a platform length, the posterior support shell having an inner posterior shell surface and an outer posterior shell surface, the posterior support shell being sized and shaped to receive the posterior portion of a user's lower leg and tarsal region, the plantar support platform being sized and shaped to support the plantar portion of a user's foot, the posterior support shell height terminating proximally in a proximal flared posterior shell brim, the posterior support shell height terminating distally in a tarsal support structure, the tarsal support structure comprising a medial tarsal support portion, a lateral tarsal support portion, and a heel support portion intermediate the medial tarsal support portion and lateral support portion, the medial tarsal support portion and the lateral tarsal support portion extending ventrally to a point intermediate the platform length, the proximal flared posterior shell brim being spatially located for fitted placement in distal adjacency to the fibular head of a user's lower leg, the posterior support shell having a circumferential corrugated rib structure intermediate the posterior support shell height, the plantar support platform having a superior surface and an inferior surface, the plantar support platform further comprising at least one ulcer-protecting hollow, the hollow being spatially located for fitted placement in inferior adjacency to a user's diabetic plantar ulcer, the hollow for transferring a user's weight away from the plantar ulcer thus facilitating plantar ulcer treatment,
a rigid, anterior support shell for lateral hinged attachment to the posterior support shell, the anterior support shell having an inner anterior support shell surface and an outer anterior support shell surface, the anterior support shell for receiving the anterior, proximal portion of a user's lower leg, the anterior support shell having a proximal flared anterior shell brim and a distal flared anterior shell rim, the proximal flared anterior shell brim being spatially located for fitted placement in distal adjacency to the fibular head of the user's leg, the anterior support shell further comprising a plurality of securing strap receiving loops securely attached to the outer anterior support shell surface, a flexible polyethylene hinge member for hingedly attaching the anterior support shell to the posterior support shell, the hinge member having an inner hinge surface and an outer hinge surface, the hinge member having a posterior hinge portion and an anterior hinge portion, the outer hinge surface of the anterior hinge portion being securely fastened to the lateral most edge of the inner anterior support shell surface, the inner hinge surface of the posterior hinge portion being securely fastened to the lateral most edge of the outer posterior support shell surface, thus hingedly attaching the anterior support shell to the posterior support shell such that the proximal flared anterior shell brim and proximal flared posterior shell brim lie in substantially the same plane and such that the distal flared anterior shell brim and circumferential corrugated rib structure lie in substantially the same plane, the circumferential corrugated rib structure for increasing structural strength of the posterior support shell and for guiding placement of the anterior support shell; and
a plurality of securing straps, the securing straps each having an inner strap surface and an outer strap surface, the outer strap surface further comprising hook and loop fastening means, the securing straps each having a posterior support shell attachment end and a securing strap feed end, the securing strap feed ends each being fed through the securing strap receiving loops for securing the anterior support shell in fixed, weight-bearing relation about the proximal, anterior portion of the user's lower leg.

2. The orthotic combination of claim 1 wherein posterior support shell padding is attached to the inner posterior support shell surface for alleviating skin irritation of the posterior portion of a user's lower leg and tarsal region and for maintaining total contact; anterior support shell padding is attached to the inner anterior support shell surface for alleviating skin irritation of the anterior, proximal portion of a user's lower leg and for maintaining total contact and for relieving bony prominences; and planter support platform padding is attached to the plantar support platform.

3. The orthotic combination of claim 2 wherein the plantar support platform is contoured to conform to the planter surface of a user's foot, the plantar support platform comprising a first anterior segment to support the toes of the foot, a second anterior segment to support the metatarsal heads of the foot, an intermediate sole segment to support the arch of the foot, and a posterior segment to support the heel of the foot.

4. The orthotic combination of claim 3 wherein the L-shaped support member comprises molded polypropylene of about 3/16 inch thickness and the anterior support shell comprises molded polypropylene of about 1/8 inch thickness.

5. The orthotic combination of claim 4 wherein custom alignment wedges are used in combination with the orthosis.

6. An orthosis for the treatment of plantar ulcers, the orthosis comprising;

a rigid, substantially L-shaped support member, the L-shaped support member comprising a substantially vertical, posterior support shell and a substantially horizontal, plantar support platform, the posterior support shell having a posterior shell height and the plantar support platform having a platform length, the posterior support shell having an inner posterior shell surface and an outer posterior shell surface, the posterior support shell having a first posterior shell edge and a second posterior shell edge opposite the first posterior shell edge, the posterior support shell being sized and shaped to receive the posterior portion of a user's lower leg and tarsal region, the plantar support platform being sized and shaped to support the plantar portion of a user's foot, the posterior support shell height terminating proximally in a proximal flared posterior shell brim, the posterior support shell height terminating distally in a tarsal support structure, the tarsal support structure comprising a medial tarsal support portion, a lateral tarsal support portion, and a heel support portion intermediate the medial tarsal support portion and lateral support portion, the medial tarsal support portion and the lateral tarsal support portion extending ventrally to a point intermediate the platform length, the proximal flared posterior shell brim being spatially located for fitted placement in distal adjacency to the fibular head of a user's lower leg, the plantar support platform having a superior surface and an inferior surface, the planter support platform further comprising an ulcer-protecting hollow, the hollow being spatially located for fitted placement in inferior adjacency to a user's plantar ulcer, the hollow for transferring a user's weight away from the plantar ulcer thus facilitating plantar ulcer treatment;

a rigid, anterior support shell for hinged attachment to the posterior support shell, the anterior support shell having an inner anterior support shell surface and an outer anterior support shell surface, the anterior support shell having a first anterior shell edge and a second anterior shell edge opposite the first anterior shell edge, the anterior support shell for receiving the anterior, proximal portion of a user's lower leg, the anterior support shell having a proximal flared anterior shell brim and a distal flared anterior shell brim, the proximal flared anterior shell brim being spatially located for fitted placement in distal adjacency to the fibular head of the user's lower leg, the anterior support shell further comprising at least one securing means receiving structure securely attached to the outer anterior support shell surface;

a circumferential corrugated rib structure intermediate the posterior support shell height for increasing structural strength of the posterior support shell and for guiding placement of anterior support shell such that the proximal flared anterior shell brim and proximal flared posterior shell brim lie in substantially the same, substantially horizontal plane and such that the distal flared anterior shell brim and circumferential corrugated rib structure lie in substantially the same, substantially horizontal plane;

hinge means for hingedly attaching the anterior support shell to the posterior support shell, the hinge means having a posterior hinge portion and an anterior hinge portion, the anterior hinge portion being securely fastened to the first anterior shell I edge, the posterior hinge portion being securely fastened to the first posterior shell edge, thus hingedly attaching the anterior support shell to the posterior support shell; and securing means for operatively engaging the securing means receiving structure, thus securing the anterior support shell in fixed, weight-bearing relation about the proximal, anterior portion of a user's leg.

7. The orthosis of claim 6 wherein the hinge means is further defined by comprising a flexible polyethylene hinge member, the hinge member hingedly attaching the anterior support shell to the posterior support shell such that the proximal flared anterior shell brim and proximal flared posterior shelf bum lie in substantially the same plane and such that the distal flared anterior shell brim and circumferential corrugated rib structure lie in substantially the same plane.

8. The orthosis of claim 7 wherein the hinge member has an inner hinge surface and an outer hinge surface, the outer hinge surface of the anterior hinge portion being securely fastened to the inner anterior support shell surface, the inner hinge surface of the posterior hinge portion being securely fastened to the outer posterior support shell surface.

9. The orthosis of claim 6 wherein the first anterior shell edge is the lateral most edge of the anterior support shell; the second anterior shell edge is the medial most edge of the anterior support shell; the first posterior shell edge is the lateral most edge of the posterior support shell; and the second posterior shell edge is the medial most edge of the posterior support shell.

10. The orthosis of claim 6 wherein the securing means is defined by further comprising at least one securing strap and the securing means receiving structure is further defined by comprising at least one securing strap receiving loop, the securing strap having an inner strap surface and an outer strap surface, the outer strap surface further comprising hook and loop fastening means, the securing strap having a posterior support shell attachment end and a securing strap feed end, the securing strap feed end being fed through the securing strap receiving loop for securing the anterior support shell in fixed, weight-bearing relation about the proximal portion of the user's lower leg.

11. The orthosis of claim 6 wherein posterior support shell padding is attached to the inner posterior support shell surface for alleviating skin irritation of the posterior portion of a user's lower leg and tarsal region and for maintaining total contact; anterior support shell padding is attached to the inner anterior support shell surface for alleviating skin irritation of the anterior, proximal portion of a user's lower leg and for maintaining total contact and for relieving bony prominences; and plantar support platform padding is attached to the plantar support platform.

12. The orthosis of claim 6 wherein the L-shaped support member comprises molded polypropylene of about 3/16 inch thickness and the anterior support shell comprises molded polypropylene of about 1/8 inch thickness.

13. An orthosis for the treatment of diabetic plantar ulcers, the orthosis comprising:

a substantially rigid, substantially L-shaped support member, the L-shaped support member comprising a substantially vertical, continuously-formed, posterior support shell and a substantially horizontal, continuously-formed, plantar support platform, the posterior support shell having a posterior shell height and the plantar support platform having a platform length, the posterior support shell having an inner posterior shell surface and an outer posterior shell surface, the posterior support shell being sized and shaped to receive all posterior portions of a user's lower leg and tarsal region, the plantar support platform being sized and shaped to support the plantar portion of a user's foot, the posterior support shell height terminating proximally in a proximal flared posterior shell brim, the posterior support shell height terminating distally in a tarsal support structure, the tarsal support structure comprising a medial tarsal support portion, a lateral tarsal support portion, and a heel support portion intermediate the medial tarsal support portion and lateral support portion, the medial tarsal support portion and the lateral tarsal support portion extending ventrally to a point intermediate the platform length, the proximal flared posterior shell brim being spatially located for fitted placement in distal adjacency to the fibular head of a user's lower leg, the posterior support shell having a circumferential corrugated rib structure intermediate the posterior support shell height, the plantar support platform having a superior platform surface and an inferior platform surface, the plantar support platform further comprising at least one substantially rigid, integrally-formed, ulcer-protecting hollow, the hollow having a superior hollow surface and an inferior hollow surface, the superior hollow surface being continuous with the superior platform surface and the inferior hollow surface being continuous with the inferior platform surface, the hollow being spatially located for fitted placement in inferior adjacency to a user's diabetic plantar ulcer, the superior hollow surface being spaced from the user's diabetic plantar ulcer, the hollow for transferring a user's weight away from the plantar ulcer thus facilitating plantar ulcer treatment, a substantially rigid, anterior support shell for lateral hinged attachment to the posterior support shell, the anterior support shell having an inner anterior support shell surface and an outer anterior support shell surface, the anterior support shell for receiving the anterior, proximal portion of a user's lower leg, the anterior support shell having a proximal flared anterior shell brim and a distal flared anterior shell rim, the proximal flared anterior shell brim being spatially located for fitted placement in distal adjacency to the fibular head of the user's leg, the anterior support shell further comprising a plurality of securing strap receiving loops securely attached to the outer anterior support shell surface, a flexible polyethylene hinge member for hingedly attaching the anterior support shell to the posterior support shell, the hinge member having an inner hinge surface and an outer hinge surface, the hinge member having a posterior hinge portion and an anterior hinge portion, the outer hinge surface of the anterior hinge portion being securely fastened to the lateral most edge of the inner anterior support shell surface, the inner hinge surface of the posterior hinge portion being securely fastened to the lateral most edge of the outer posterior support shell surface, thus hingedly attaching the anterior support shell to the posterior support shell such that the proximal flared anterior shell brim and proximal flared posterior shell brim lie in substantially the same, substantially horizontal plane and such that the distal flared anterior shell brim and circumferential corrugated rib structure lie in substantially the same, substantially horiztonal plane, the circumferential corrugated rib structure for increasing structural strength of the posterior support shell and for guiding placement of the anterior support shell; and a plurality of securing straps, the securing straps each having an inner strap surface and an outer strap surface, the outer strap surface further comprising hook and loop fastening means, the securing straps each having a posterior support shell attachment end and a securing strap feed end, the securing strap feed ends each being fed through the securing strap receiving loops for securing the anterior support shell in fixed, weight-bearing relation about the proximal, anterior portion of the user's lower leg.

14. The orthosis of claim 13 wherein posterior support shell padding is attached to the inner posterior support shell surface for alleviating skin irritation of the posterior portion of a user's lower leg and tarsal region and for maintaining total contact; anterior support shell padding is attached to the inner anterior support shell surface for alleviating skin irritation of the anterior, proximal portion of a user's lower leg and for maintaining total contact and for relieving bony prominences; and plantar support platform padding is attached to the plantar support platform.

15. The orthosis s of claim 13 wherein the plantar support platform is contoured to conform to the plantar surface of a user's foot, the plantar support platform comprising a first anterior segment to support the toes of the foot, a second anterior segment to support the metatarsal heads of the foot, an intermediate sole segment to support the arch of the foot, and a posterior segment to support the heel of the foot.

16. The orthosis of claim 13 wherein the L-shaped support member comprises molded polypropylene of about 3/16 inch thickness and the anterior support shell comprises molded polypropylene of about 1/8 inch thickness.

17. The orthosis of claim 13 wherein custom alignment wedges are used in combination with the orthosis to provide stability therefor.

* * * * *